(12) United States Patent
Loy

(10) Patent No.: US 6,485,410 B1
(45) Date of Patent: Nov. 26, 2002

(54) HYSTEROSCOPE PORT AND METHODS

(75) Inventor: Randall A. Loy, Longwood, FL (US)

(73) Assignee: Synergyn Technologies, Inc., Longwood, FL (US)

( * ) Notice: Subject to any disclaimer, the term of this patent is extended or adjusted under 35 U.S.C. 154(b) by 0 days.

(21) Appl. No.: 09/260,901

(22) Filed: Mar. 2, 1999

Related U.S. Application Data

(60) Provisional application No. 60/107,050, filed on Nov. 4, 1998.

(51) Int. Cl.⁷ .............................................. A61B 1/307
(52) U.S. Cl. ...................... 600/135; 600/115; 600/116; 600/114; 604/96.01; 604/97.01; 604/515; 604/509; 606/193
(58) Field of Search ................................ 600/135, 116, 600/114, 115, 153, 156, 120; 606/192, 193; 604/96, 97, 509, 515

(56) References Cited

U.S. PATENT DOCUMENTS

| | | | |
|---|---|---|---|
| 4,198,981 A | | 4/1980 | Sinnreich |
| 4,664,114 A | | 5/1987 | Ghodsian |
| 4,692,200 A | * | 9/1987 | Powell .................. 156/389 |
| 4,994,070 A | | 2/1991 | Waters |
| 5,104,377 A | | 4/1992 | Levine |
| 5,217,466 A | * | 6/1993 | Hasson ................. 606/119 |
| 5,338,297 A | | 8/1994 | Kocur et al. |
| 5,372,584 A | | 12/1994 | Zink et al. |
| 5,425,712 A | * | 6/1995 | Goodin .................. 604/96 |
| 5,540,658 A | * | 7/1996 | Evans et al. ............. 604/101 |
| 5,545,138 A | * | 8/1996 | Fugoso et al. ........... 604/102 |
| 5,624,399 A | | 4/1997 | Ackerman |
| 5,707,382 A | | 1/1998 | Sierocuk et al. |
| 5,716,325 A | | 2/1998 | Bonutti |
| 5,722,983 A | * | 3/1998 | Van Der Weegen ........ 606/193 |
| 5,743,852 A | | 4/1998 | Johnson |
| 5,817,123 A | | 10/1998 | Kieturakis et al. |
| 5,823,945 A | | 10/1998 | Moll et al. |
| 5,935,098 A | * | 8/1999 | Blasdell et al. .............. 604/55 |
| 5,951,584 A | * | 9/1999 | Hermann .................. 606/194 |

* cited by examiner

Primary Examiner—Linda C. M. Dvorak
Assistant Examiner—Jocelyn Ram
(74) Attorney, Agent, or Firm—Allen, Dyer, Doppelt, Milbrath & Gilchrist, P.A.

(57) ABSTRACT

The hysteroscope port includes a cylindrical cannula dimensioned for insertion through a vagina to penetrate a cervix. A balloon element having a nonsmooth surface is positioned adjacent the distal end of the cannula for dilating the cervix and for maintaining the cervix in a dilated state. The balloon is inflatable between a narrowed insertion and withdrawal position and an expanded dilatation position. An introducer's distal portion is dimensioned for insertion through the cannula's lumen and is sufficiently long to extend beyond the cannula's distal end. The introducer's distal tip is tapered and smooth for ease of insertion. The introducer's proximal portion protrudes from the cannula's proximal opening for being grasped for insertion into and removal from the cannula.

22 Claims, 1 Drawing Sheet

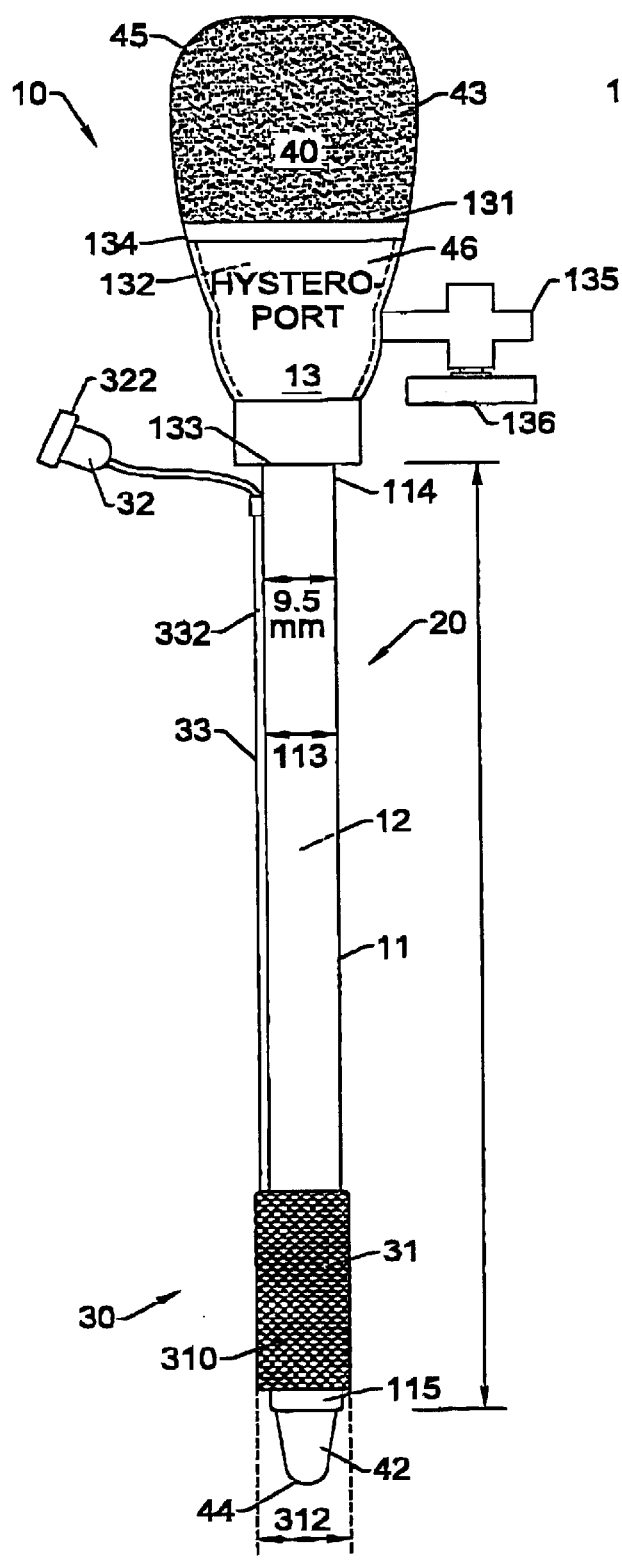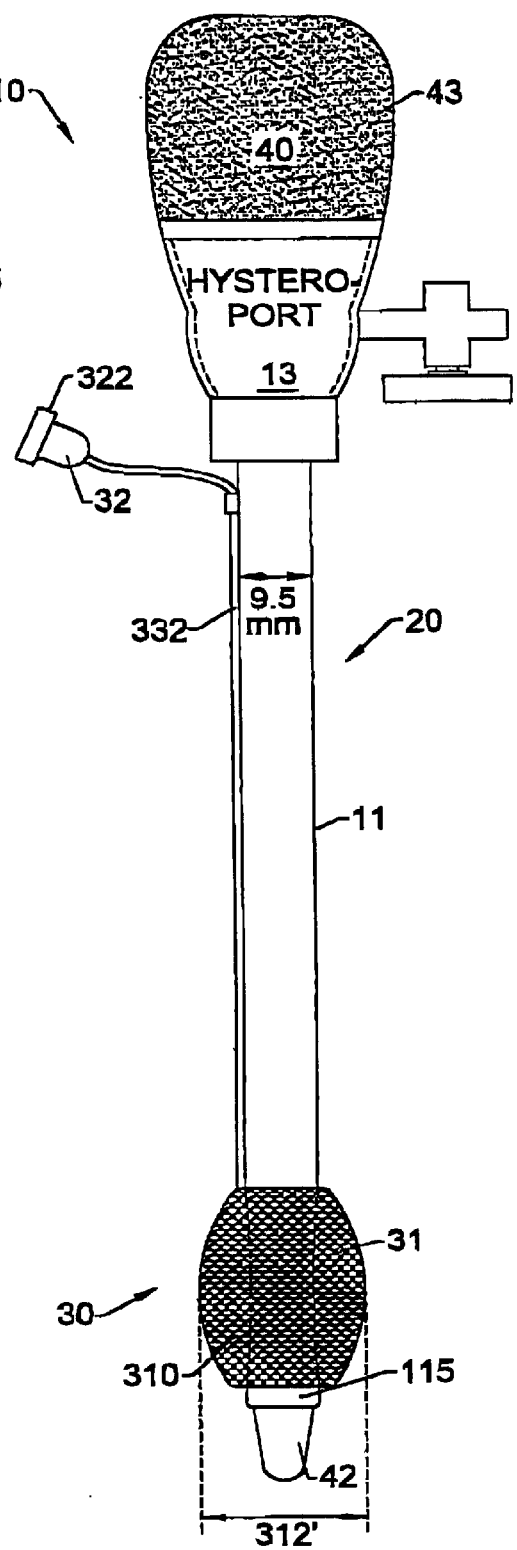

HYSTEROSCOPE PORT AND METHODS

CROSS-REFERENCE TO RELATED APPLICATION

This application claims priority from copending provisional application Ser. No. 60/107,050, "Hysteroscope Port and Methods," filed Nov. 4, 1998.

BACKGROUND OF THE INVENTION

1. Field of the Invention

The present invention relates to surgical devices and methods, and, more particularly, to devices and methods for providing an instrument portal into the uterus.

2. Description of Related Art

The evolution of surgical procedures has been along a path of decreasing invasiveness. Such changes have been advanced by the introduction of systems permitting external visualization of procedures and devices that are externally manipulable.

In the obstetrical/gynecological arena, for example, access into the uterus and fallopian tubes can be achieved by inserting a speculum into the vagina and performing a dilatation of the cervix if necessary or desired, such as with the use of cervical clamps. Visualization and manipulation instruments can then be inserted through the speculum opening to carry out a desired procedure. Among the devices currently used is a flexible hysteroscope, which may include visualization means such as fiber optic illumination and viewing elements and forceps-type grasping jaws.

A particular problem with the current devices and methods, however, is that multiple placements of the speculum are usually required, and the cervix is difficult to restrain in a dilated position, as it is biased to a closed position.

Laparoscopic trocars are known in the art for insertion through tissue to obtain access to an internal organ. Their design is predicated on the cylindrical portion of the trocar remaining in place in the skin, and it is typically desired to keep the hole in the skin as small as possible. Such trocars have been designed with balloons, but these balloons are for retaining that section of the trocar within the body's interior.

SUMMARY OF THE INVENTION

It is therefore an object of the present invention to provide a device for passing an instrument into the uterus through the cervix.

It is an additional object to provide such a device that retains the cervix in a dilated state.

It is a further object to provide such a device whose insertion is not damaging to the bodily tissue.

It is another object to provide a method of performing a gynecological procedure.

An additional object is to provide a method of making a device for passing instrument into a uterus.

These objects and others are achieved by the device and methods of the present invention. The device comprises an elongated generally cylindrical cannula having a proximal and a distal opening and a lumen therebetween. The cannula is dimensioned for insertion through a vagina to penetrate a cervix. Means are positioned adjacent the distal end of the cannula for dilating the cervix and for maintaining the cervix in a dilated state. The dilatation means are manipulable between a narrowed insertion and withdrawal position and an expanded dilatation position. The dilatation means have a surface adapted to resist slippage against the cervical surface.

The device also comprises an introducer having a generally cylindrical distal portion dimensioned for insertion through the cannula lumen and sufficiently long to extend beyond the cannula's distal end. The introducer's distal tip is tapered for ease of insertion, but is preferably smooth to prevent tissue damage. The introducer also has a proximal portion adapted to protrude from the cannula's proximal opening and having means for being grasped for insertion into and removal from the cannula.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 1 is a side perspective view the device of the present invention in the insertion configuration.

FIG. 2 is a side perspective view of the device in the dilatation configuration.

DETAILED DESCRIPTION OF THE PREFERRED EMBODIMENTS

A description of the preferred embodiments of the present invention will now be presented with reference to FIGS. 1 and 2.

The hysteroscope port 10 comprises three elements: a cannula 20, an inflator mechanism 30, and an introducer 40.

The cannula 20 comprises a generally cylindrical distal portion 11 having a length 112 sufficient to penetrate a vagina and extend beyond the cervix and a diameter 113 dimensioned for comfortable insertion, e.g., 9.5 mm, although this is not intended as a limitation. The lumen 12 is dimensioned to permit the passage of a desired instrument therethrough.

Adjacent the distal portion's 11 proximal end 114 is a portal element 13 that has a proximal opening 131 communicating with an entry space 132 that communicates at its distal end 133 with the lumen 12. The portal element 13 tapers outward from its distal end 133 to its proximal end 134. Within the entry space 132 is affixed means for isolating the lumen from the exterior environment, which has means for admitting a desired instrument. These means may comprise, for example, means as are known in the art such as a flapper valve or rubber seal (not shown), although these are not intended as limitations.

Extending radially from the side of the portal element 13 is a valved influx port 135 through which a fluid such as distension medium may be added into the entry space 132. Handle 136 operates a valve for permitting or preventing access through the port 135.

The inflator mechanism 30 comprises a generally annular inflatable balloon member 31 affixed in surrounding relation to the cannula's distal portion 11 adjacent the distal end 115. The balloon 31 preferably has a coarse outer surface 310 adapted to frictionally engage the cervix and to this end may be, for example, striated and/or ribbed.

Inflation of the balloon 31 is achieved by injecting a fluid through an inflation port 32 having an opening 322 communicating with the lumen 332 of a line 33 that is positioned adjacent at least a portion of the length of the cannula's distal portion 11. The line's lumen 332 in turn communicates with the interior of the balloon 31 so that inflation may be achieved from an insertion configuration (FIG. 1), wherein the balloon 31 has substantially the same diameter 312 as that 113 of the cannula's distal portion 11, to a dilatation configuration (FIG. 2), wherein the balloon 31 is inflated so that its outer surface bulges to a larger diameter 312' than that 113 of the cannula's distal portion 11.

The device 10 further comprises an introducer 40 for facilitating the insertion of the cannula 20 into position. The introducer 40 includes a generally cylindrical distal portion (not shown; interior to cannula distal portion 11) dimensioned for insertion through the cannula's lumen 12. The distal tip 42 tapers to a blunt end 44 to ease insertion without damaging tissue. Preferably at least the distal tip 42 comprises a material sufficiently resilient, such as a rubber or plastic, also to avoid damaging tissue.

The introducer's proximal portion 43 is widened to prevent its passage into the cannula's lumen 12 and has a distal section 46 dimensioned to fit within the portal's entry space 132. The proximal section 45 of the proximal portion 43 is dimensioned to protrude proximal of the portal 13 so that it may be gripped for removal from the cannula 20.

The method of using the device 10 comprises the steps of inserting the device 10, with the introducer 40 in place inside the cannula 20, into a vagina sufficiently far that the introducer's distal tip 42 protrudes into the uterus and the balloon 31, in the insertion configuration, spans the cervix.

By forcing a fluid under pressure through the inflation port's opening 322 and through the line 33 into the balloon 31 until it is sufficiently inflated to dilate the cervix (FIG. 2), the coarse surface 310 frictionally engaging the cervix to retain it thereagainst. Next the introducer 40 is removed from the cannula 20.

Once the desired surgical procedure has been completed, the balloon 31 is deflated by releasing the pressure from the inflation port's opening 322, and the cannula 20 is removed.

It may be appreciated by one skilled in the art that additional embodiments may be contemplated, including various other devices for achieving dilatation and for achieving frictional engagement with the cervical wall.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

What is claimed is:

1. A hysteroscope comprising:
    a cannula member having an elongated, generally cylindrical distal portion having a lumen extending between a proximal opening and a distal opening, the distal portion dimensioned for insertion through a human vagina and into a cervix uteri, the distal opening extending therebeyond; and
    an inflatable member affixed to the cannula member generally adjacent the distal opening and manipulatable between a narrowed position for insertion and withdrawal and an expanded position for cervical dilatation, the inflatable member having a nonsmooth outer surface adapted to frictionally engage a cervical surface for resisting slippage thereagainst.

2. The hysteroscope recited in claim 1, wherein the lumen is dimensioned sufficiently large to permit a passage of a desired instrument therethrough.

3. The hysteroscope recited in claim 1, wherein the cannula member further comprises a portal element joining the distal portion at a proximal end thereof, the portal element having a wall and a proximal opening leading to an entry space in communication with the distal portion lumen at a distal end, the portal element tapering outward in a proximal direction.

4. The hysteroscope recited in claim 3, further comprising an isolation element affixed within the entry space adapted to sealindy surround an instrument passed therethrough.

5. The hysteroscope recited in claim 4, wherein the isolation element is selected from a group consisting of a flapper valve and a rubber seal.

6. The hysteroscope recited in claim 3, further comprising fluid introduction means extending through the portal element wall into the entry space.

7. The hysteroscope recited in claim 6, wherein the fluid introduction means comprises valve means operable in an open position to permit fluid movement therethrough and operable in a closed position to prevent fluid movement therethrough.

8. The hysteroscope recited in claim 1, wherein the inflatable member comprises a balloon member affixed in at least partially surrounding relation to the distal portion of the cannula member adjacent a distal end thereof.

9. The hysteroscope recited in claim 1, wherein the inflatable member comprises a generally annular balloon member affixed in surrounding relation to the distal portion of the cannula member adjacent a distal end thereof.

10. The hysteroscope recited in claim 1, wherein the inflatable member nonsmooth outer surface has at least one of a striated or a ribbed feature thereon.

11. The hysteroscope recited in claim 1, further comprising means for inflating the inflatable member in communication with an interior of the inflatable member.

12. The hysteroscope recited in claim 11, wherein the inflating means comprises a line positioned along an outside of the cannula member distal portion, the line having a lumen extending from a proximal end to a distal end, the distal end in communication with the inflatable member interior.

13. The hysteroscope recited in claim 12, wherein the inflating means further comprises an inflation port affixed at the line proximal end and having an opening communicating with the line lumen, the port adapted to receive a fluid source.

14. The hysteroscope recited in claim 13, wherein the inflating means further comprises a removable cap dimensioned to sealingly engage the inflation port for preventing fluid passage therethrough.

15. The hysteroscope recited in claim 1, further comprising means for facilitating an introduction of the cannula distal portion into the vagina, the facilitating means removable within and having a portion dimensioned to extend distally beyond the cannula member distal end.

16. The hysteroscope recited in claim 15, wherein the introduction means comprises an introducer having a generally cylindrical distal portion dimensioned for insertion into the cannula member lumen and a distal tip having a generally blunt end for avoiding tissue damage thereby, the distal tip adapted to extend distally beyond the cannula member distal end, the introducer comprising a material having sufficient resiliency to avoid tissue damage.

17. The hysteroscope recited in claim 16, wherein the introducer further has a proximal portion dimensioned to prevent passage into the cannula member lumen and adapted for gripping to achieve a removal therefrom.

18. The hysteroscope recited in claim 15, wherein the dilatation means comprises an inflatable, generally annular balloon member affixed in surrounding relation to the distal portion of the cannula member adjacent a distal end thereof, the balloon member having a nonsmooth outer surface adapted to frictionally engage the cervical surface.

19. A method for dilating a human cervix uteri comprising the steps of:

inserting a generally cylindrical cannula member through a human vaginal canal into a cervix uteri, a distal end of the cannula member extending beyond the cervix uteri; and inflating a balloon member affixed about the cannula member in a position adjacent the distal end thereof, the balloon member having a nonsmooth surface adapted to frictionally engage the cervix uteri.

20. The method recited in claim 19, further comprising the step of inserting a blunt-tipped introducer into a lumen of the cannula member, the blunt tip extending beyond a distal end of the cannula member, and wherein the insertion step comprises inserting the cannula member/introducer combination, the blunt tip for diminishing a chance for tissue damage.

21. The method recited in claim 19, further comprising the step of introducing a distension fluid through a lumen of the cannula member following the inflating step.

22. The method recited in claim 19, further comprising the steps, following the inflating step, of:

inserting an instrument through a lumen of the cannula member;

performing a desired procedure with the instrument;

withdrawing the instrument from the cannula member lumen;

deflating the balloon member; and withdrawing the cannula member from the cervix uteri and the vagina.

* * * * *